(12) United States Patent
Barbaric et al.

(10) Patent No.: US 11,406,136 B2
(45) Date of Patent: Aug. 9, 2022

(54) METHODS AND SYSTEMS FOR VAPORIZER SECURITY AND TRACEABILITY MANAGEMENT

(71) Applicant: Airgraft Inc., Montreal (CA)

(72) Inventors: Mladen Barbaric, Westmount (CA); Yuhao Liao, Montreal (CA); Luca Corbellini, Montreal (CA); Nathan Songa Yapi, Montreal (CA); Sungmoon Kim, Brossard (CA); Bong geun Kim, Candiac (CA); Chongchun Moon, La Prairei (CA)

(73) Assignee: Airgraft Inc., Montreal (CA)

( * ) Notice: Subject to any disclaimer, the term of this patent is extended or adjusted under 35 U.S.C. 154(b) by 0 days.

(21) Appl. No.: 16/911,011

(22) Filed: Jun. 24, 2020

(65) Prior Publication Data

US 2021/0145076 A1    May 20, 2021

Related U.S. Application Data

(63) Continuation of application No. 16/575,318, filed on Sep. 18, 2019, now Pat. No. 10,721,971.

(Continued)

(51) Int. Cl.
*A01G 13/06*        (2006.01)
*A24F 40/70*        (2020.01)
(Continued)

(52) U.S. Cl.
CPC .............. *A24F 40/70* (2020.01); *G06F 9/542* (2013.01); *G06F 16/9035* (2019.01);
(Continued)

(58) Field of Classification Search
CPC ........ A24F 47/008; A24F 40/10; A24F 40/40; A24F 40/53; A24F 40/60; A24F 40/65;
(Continued)

(56) References Cited

U.S. PATENT DOCUMENTS

| D299,066 S | 12/1988 | Newell et al. |
| 4,947,874 A | 8/1990 | Brooks et al. |

(Continued)

FOREIGN PATENT DOCUMENTS

| CA | 2805553 C | 1/2015 |
| CN | 204466911 U | 7/2015 |

(Continued)

OTHER PUBLICATIONS

International Search Report issued for PCT/CA2019/051326 dated Nov. 21, 2019.

(Continued)

*Primary Examiner* — Hung D Nguyen
(74) *Attorney, Agent, or Firm* — Cooley LLP

(57) ABSTRACT

In some embodiments, a processor-implement method includes receiving a fill completion message including formulation and capsule identifiers from a fill station. The method also includes receiving a registration request including a vaporizer identifier and a compute device or user identifier from a compute device. The registration request is verified, and a registration confirmation message is sent to the compute device. The method also includes receiving a capsule attach event detection message including the capsule identifier, the vaporizer identifier, and at least one of the identifier of the compute device or the identifier of the user. A validity of the capsule attach event detection message is evaluated. If the capsule attach event detection message is valid, an unlock message is sent to the compute device or a vaporizer, and if the capsule attach event detection message is valid, an alert is sent to the compute device or the vaporizer.

20 Claims, 6 Drawing Sheets

Related U.S. Application Data

(60) Provisional application No. 62/732,860, filed on Sep. 18, 2018.

(51) Int. Cl.
| | |
|---|---|
| *G06F 16/9035* | (2019.01) |
| *G06F 21/34* | (2013.01) |
| *H04W 4/029* | (2018.01) |
| *H04L 9/32* | (2006.01) |
| *H04L 9/30* | (2006.01) |
| *G06F 9/54* | (2006.01) |

(52) U.S. Cl.
CPC ............... *G06F 21/34* (2013.01); *H04L 9/30* (2013.01); *H04L 9/3247* (2013.01); *H04W 4/029* (2018.02)

(58) Field of Classification Search
CPC .... A24F 40/70; H04W 4/029; G06F 16/9035; G06F 9/542; G06F 21/34; H04L 9/30; H04L 9/3247
USPC ....... 392/386, 387, 390, 391, 394, 395, 397, 392/398, 403, 404, 405, 406; 131/273, 131/328, 329
See application file for complete search history.

(56) References Cited

U.S. PATENT DOCUMENTS

| | | | |
|---|---|---|---|
| 5,044,550 A | 9/1991 | Lamm | |
| 5,135,009 A | 8/1992 | Muller et al. | |
| 5,564,442 A | 10/1996 | MacDonald et al. | |
| D449,404 S | 10/2001 | Emery | |
| 6,513,524 B1 | 2/2003 | Storz | |
| 6,532,965 B1 | 3/2003 | Abhulimen et al. | |
| 7,096,896 B2 | 8/2006 | Py | |
| D610,303 S | 2/2010 | Valle | |
| 7,832,410 B2 | 11/2010 | Hon | |
| D634,892 S | 3/2011 | Hein | |
| 7,997,280 B2 | 8/2011 | Rosenthal | |
| D677,000 S | 2/2013 | Liu | |
| D683,844 S | 6/2013 | Andrade et al. | |
| 8,499,766 B1 | 8/2013 | Newton | |
| D689,818 S | 9/2013 | Sasada | |
| 8,528,569 B1 | 9/2013 | Newton | |
| 8,689,804 B2 * | 4/2014 | Fernando ................ A24F 40/53 131/271 |
| 8,707,965 B2 | 4/2014 | Newton | |
| 8,733,346 B2 | 5/2014 | Rinker | |
| 8,897,628 B2 | 11/2014 | Conley et al. | |
| 8,991,402 B2 | 3/2015 | Bowen et al. | |
| 9,308,336 B2 | 4/2016 | Newton | |
| D762,003 S | 7/2016 | Lomeli | |
| 9,408,416 B2 | 8/2016 | Monsees et al. | |
| D765,908 S | 9/2016 | Zahr et al. | |
| D770,090 S | 10/2016 | Zahr et al. | |
| D770,091 S | 10/2016 | Zahr et al. | |
| D771,308 S | 11/2016 | Saydar et al. | |
| D776,338 S | 1/2017 | Lomeli | |
| 9,549,573 B2 | 1/2017 | Monsees et al. | |
| D778,235 S | 2/2017 | Geier et al. | |
| 9,596,887 B2 | 3/2017 | Newton | |
| 9,717,276 B2 | 8/2017 | Brammer et al. | |
| 9,820,509 B2 | 11/2017 | Newton et al. | |
| 9,894,938 B2 | 2/2018 | Vick et al. | |
| D812,289 S | 3/2018 | Ward et al. | |
| 10,058,130 B2 | 3/2018 | Monsees et al. | |
| 10,070,669 B2 | 3/2018 | Monsees et al. | |
| D816,267 S | 4/2018 | Fornarelli | |
| 9,999,250 B2 | 6/2018 | Minskoff et al. | |
| D825,102 S | 8/2018 | Bowen et al. | |
| D827,117 S | 8/2018 | Rigbi | |
| 10,045,567 B2 | 8/2018 | Monsees et al. | |
| 10,045,568 B2 | 8/2018 | Monsees et al. | |
| 10,058,124 B2 | 8/2018 | Monsees et al. | |
| 10,058,129 B2 | 8/2018 | Monsees et al. | |
| 10,076,139 B2 | 9/2018 | Monsees et al. | |
| 10,104,915 B2 | 10/2018 | Bowen et al. | |
| 10,111,470 B2 | 10/2018 | Monsees et al. | |
| 10,117,465 B2 | 11/2018 | Monsees et al. | |
| 10,117,466 B2 | 11/2018 | Monsees et al. | |
| 10,159,282 B2 | 12/2018 | Monsees et al. | |
| 10,201,190 B2 | 2/2019 | Monsees et al. | |
| D842,536 S | 3/2019 | Bowen et al. | |
| D844,235 S | 3/2019 | Cividi | |
| D844,240 S | 3/2019 | Kauss | |
| 10,231,486 B2 | 3/2019 | Bowen et al. | |
| 10,244,793 B2 | 4/2019 | Monsees et al. | |
| 10,264,823 B2 | 4/2019 | Monsees et al. | |
| D849,996 S | 5/2019 | Duque et al. | |
| 10,279,934 B2 | 5/2019 | Christensen et al. | |
| 10,405,582 B2 | 9/2019 | Hatton et al. | |
| 10,426,196 B2 | 10/2019 | Calfee et al. | |
| 10,440,989 B2 | 10/2019 | Gardella et al. | |
| 10,524,980 B2 | 1/2020 | Naing et al. | |
| 10,721,971 B2 | 7/2020 | Barbaric et al. | |
| 2011/0277761 A1 | 11/2011 | Terry et al. | |
| 2013/0284192 A1 | 10/2013 | Peleg et al. | |
| 2013/0319439 A1 | 12/2013 | Gorelick et al. | |
| 2014/0366898 A1 | 12/2014 | Monsees et al. | |
| 2014/0378790 A1 | 12/2014 | Cohen | |
| 2015/0090280 A1 | 4/2015 | Chen | |
| 2015/0150308 A1 | 6/2015 | Monsees et al. | |
| 2015/0181945 A1 | 7/2015 | Tremblay | |
| 2015/0224268 A1 | 8/2015 | Henry et al. | |
| 2015/0296887 A1 | 10/2015 | Zhu | |
| 2015/0320116 A1 | 11/2015 | Bleloch et al. | |
| 2016/0200463 A1 | 1/2016 | Jang et al. | |
| 2016/0080535 A1 | 3/2016 | Stanimirovic et al. | |
| 2016/0128384 A1 | 5/2016 | Luciani | |
| 2016/0157524 A1 | 6/2016 | Bowen et al. | |
| 2016/0295917 A1 | 10/2016 | Malgat et al. | |
| 2016/0363917 A1 | 12/2016 | Blackley | |
| 2016/0366947 A1 | 12/2016 | Monsees et al. | |
| 2017/0042235 A1 | 2/2017 | Gorilovsky | |
| 2017/0208867 A1* | 7/2017 | Li ........................... A24F 40/65 |
| 2017/0238617 A1 | 8/2017 | Scatterday | |
| 2018/0037381 A1 | 2/2018 | White et al. | |
| 2018/0043114 A1 | 2/2018 | Bowen et al. | |
| 2018/0060873 A1 | 3/2018 | Chu | |
| 2018/0077967 A1 | 3/2018 | Hatton et al. | |
| 2018/0093054 A1 | 4/2018 | Bowen et al. | |
| 2018/0117268 A1 | 5/2018 | Selby et al. | |
| 2018/0177231 A1 | 6/2018 | Woodbine et al. | |
| 2019/0158938 A1 | 5/2019 | Bowen et al. | |
| 2019/0159519 A1 | 5/2019 | Bowen et al. | |
| 2019/0261689 A1 | 8/2019 | Bowen et al. | |

FOREIGN PATENT DOCUMENTS

| | | | |
|---|---|---|---|
| CN | 105962427 A | 9/2016 | |
| CN | 107822208 | 3/2018 | |
| CN | 110236228 A | 9/2019 | |
| EP | 2592005 A1 | 5/2013 | |
| FR | 3039039 A1 | 1/2017 | |
| WO | WO 2017/139595 A1 | 8/2017 | |
| WO | WO 2017/185051 | 10/2017 | |
| WO | WO 2017/187148 A1 | 11/2017 | |
| WO | WO 2018/024154 A1 | 2/2018 | |
| WO | WO 2019/104227 A1 | 5/2019 | |
| WO | WO 2019/126805 A1 | 6/2019 | |
| WO | WO-2019114597 A1 * | 6/2019 | ............. A24F 40/53 |
| WO | WO 2019/204812 A1 | 10/2019 | |

OTHER PUBLICATIONS

International Search Report issued for PCT/CA2019/051468 dated Dec. 19, 2019.

International Search Report issued for PCT/CA2019/051469 dated Dec. 30, 2019.

(56) References Cited

OTHER PUBLICATIONS

Extended European Search Report and Search Opinion, dated May 17, 2022, for European application No. 19861746.6 (10 total pages).

* cited by examiner

METHODS AND SYSTEMS FOR VAPORIZER SECURITY AND TRACEABILITY MANAGEMENT

CROSS-REFERENCE TO RELATED APPLICATIONS

This application is a continuation of U.S. patent application Ser. No. 16/575,318, filed Sep. 18, 2019, which claims priority to and the benefit of U.S. Provisional Application No. 62/732,860, filed Sep. 18, 2018, entitled "Methods and Systems for Vaporizer Security and Traceability Management," the entire content of each of the aforementioned applications is hereby expressly incorporated by reference for all purposes.

BACKGROUND

Electronic vapor delivery systems are increasingly popular. Such systems have been developed for inhalation-based delivery of *cannabis* components and nicotine.

SUMMARY

In some embodiments, a processor-implemented method includes receiving a fill completion message including a formulation identifier and a capsule identifier from a fill station. The method also includes receiving a registration request including a vaporizer identifier and at least one of an identifier of the compute device or an identifier of the user from a compute device. The registration request is verified, a registration record is generated and stored based on the verification, and a registration confirmation message is sent to the compute device. The method also includes receiving a capsule attach event detection message including the capsule identifier, the vaporizer identifier, and at least one of the identifier of the compute device or the identifier of the user. A validity of the capsule attach event detection message is evaluated. If the capsule attach event detection message is valid, an unlock message is sent to the compute device or a vaporizer, and if the capsule attach event detection message is invalid, an alert is sent to the compute device or the vaporizer. The alert can include a signal to cause at least one of: illumination of an indicator light of the vaporizer, emission of an audio signal from at least one of the compute device and the vaporizer, display of an alert message on an interface of the vaporizer, display of an alert message via a graphical user interface (GUI) of the compute device, or haptic feedback (e.g., vibration of the compute device).

In some embodiments, a processor-implement method includes storing, in a memory, a provenance record associating a capsule identifier with capsule fill data. A capsule attach event detection message is received at the processor and from the compute device, the capsule attach event detection message including the capsule identifier, a vaporizer identifier associated with the vaporizer, and at least one of an identifier of the compute device or an identifier of a user. The processor determines, based on the provenance record, whether the capsule attach event detection message is valid, for example by matching the capsule identifier to the provenance record. If the capsule attach event detection message is valid, an unlock message is sent from the processor to one of the compute device or a vaporizer associated with the vaporizer identifier, to unlock the vaporizer for use. If the capsule attach event detection message is not valid, an alert is sent from the processor to one of the compute device or the vaporizer.

In some embodiments, the method also includes storing, in the memory, a registration record associating the user with the compute device and the vaporizer, and the determining whether the capsule attach event detection message is valid further includes matching the vaporizer identifier and the at least one of the identifier of the compute device or the identifier of the user to the registration record.

In some embodiments, the method also includes sending a provenance message to one of the compute device or the vaporizer, to cause display of provenance data via a GUI of the one of the compute device or the vaporizer if the capsule attach event detection message is valid.

In some embodiments, an apparatus includes a processor, and a memory operably coupled to the processor and storing instructions to cause the processor to receive, from a remote compute device, a capsule attach event detection message. The capsule attach event detection message includes a capsule identifier, a vaporizer identifier, and at least one of an identifier of the remote compute device or an identifier of a user. The memory also stores instructions to cause the processor to determine, based on a registration record, whether the capsule attach event detection message is valid. The memory also stores instructions to cause the processor to send a signal from the processor to one of the compute device or a vaporizer associated with the vaporizer identifier, to unlock the vaporizer for use, if the capsule attach event detection message is valid. The memory also stores instructions to cause the processor to send an alert from the processor to one of the compute device or the vaporizer if the capsule attach event detection message is not valid.

DETAILED DESCRIPTION

As the popularity of, and commercial interest in, electronic vapor delivery systems (also referred to as "vapor devices" or "vaporizers") such as electronic cigarettes ("e-cigs") continues to grow, their manufacture and distribution is becoming more globally widespread. However, regulation is not yet finalized in many jurisdictions, and varies widely across jurisdictions. Some jurisdictions require standardization and quality control for vapor devices and their carriers (typically liquids). Moreover, counterfeit vapor devices in the marketplace present a safety hazard to consumers, and can lead to consumer mistrust and brand dilution. As such, supply chain participants such as manufacturers and distributors are incentivized to ensure safety, authenticity and traceability of their product. Systems and methods for achieving such objectives are set forth herein.

Figure 1A:
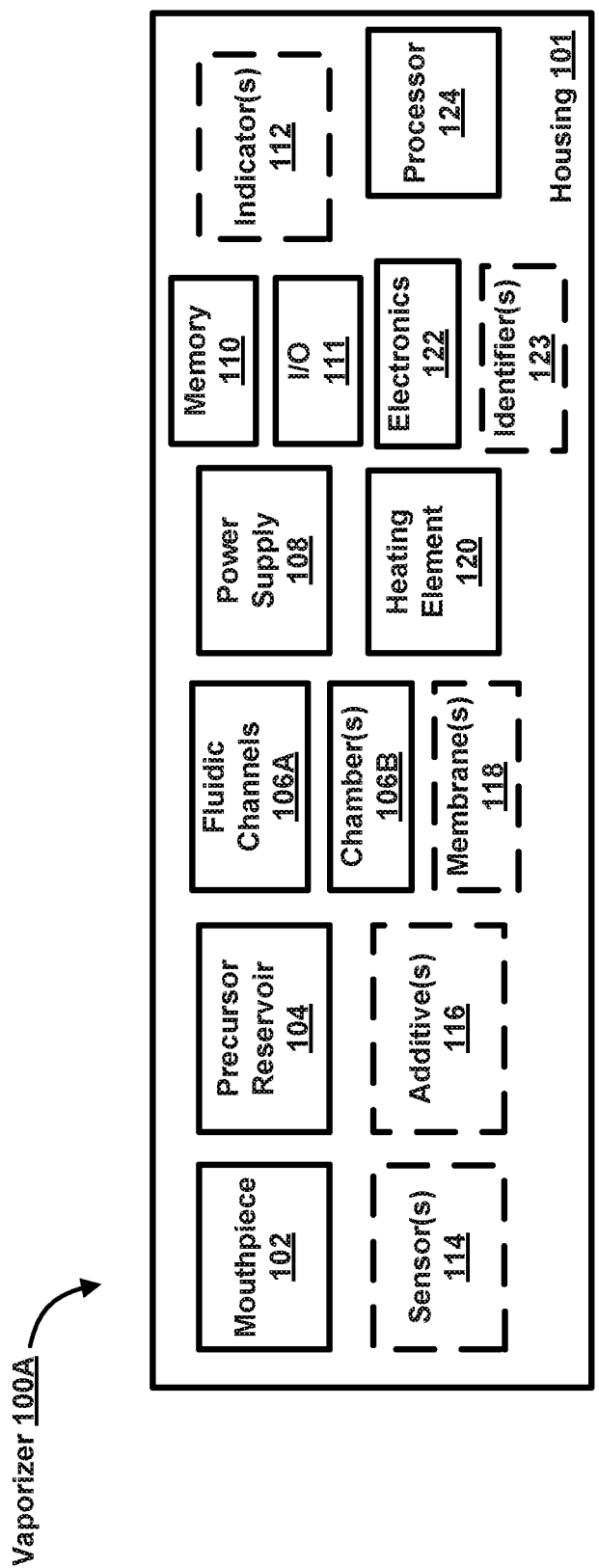
FIG. 1A is a schematic block diagram of a disposable vaporizer, according to an embodiment.

FIG. 1A is a schematic block diagram of a disposable (or "single-use") vaporizer, according to an embodiment. As shown in FIG. 1A, a disposable vaporizer 100A includes a mouthpiece 102, a precursor reservoir 104, fluidic channels 106A (e.g., microfluidics or other passageways), one or more chambers 106B, a power supply 108, memory 110, input/output module 111, a heating element 120, electronics 122, and a processor 124, all disposed within a common (e.g., monolithic) housing 101. Optionally, the disposable vaporizer 100A also includes one or more of: sensor(s) 114, additive(s) 116, membrane(s) 118, indicator(s) 112, and identifier(s) 123, also disposed within the common housing 101.

The mouthpiece 102 can comprise one or more of: ceramic, heat-resistant plastic, anodized aluminum, or any other suitable material. The power supply 108 can include any suitable battery or fuel cell, for example having high-drain characteristics. The precursor reservoir 104 can be in fluid communication with at least one of the mouthpiece, the one or more chambers 106B (e.g., vapor expansion chambers), and the fluidic channels 106A, to facilitate the triggering of carrier heating in response to a user's sucking/drawing on the mouthpiece during use, for example using a pressure sensor. Alternatively or in addition, the vaporizer 100A can be configured to heat the carrier in response to an airflow sensor signal that triggers the heating. For example, when a user draws on the mouthpiece, the airflow sensor can turn on the heating element. Alternatively or in addition, the vaporizer 100A can include a mechanical interface (e.g., a button) that the user can actuate to trigger the heating and vaporization of the carrier.

The memory 110 can include any electronic component capable of storing electronic information. The term memory may refer to various types of processor-readable media such as random access memory (RAM), read-only memory (ROM), non-volatile random access memory (NVRAM), programmable read-only memory (PROM), erasable programmable read only memory (EPROM), electrically erasable PROM (EEPROM), flash memory, magnetic or optical data storage, registers, etc. Memory is said to be in electronic communication with a processor if the processor can read information from and/or write information to the memory. Memory that is integral to a processor is in electronic communication with the processor.

The input/output module 111 can include one or more of: a push-button control for causing vapor generation, a battery indicator, an electromechanical connector for charging and/or data communication, a light source (e.g., one or more light-emitting diodes), etc. The heating element 120 can include a coil heater, rod-shaped heater, pancake heater, chemical heater, or any other heater that is sized, dimensioned, and constituted of material suitable for heating the carrier material. The electronics 122 can include one or more of: a GPS receiver, an antenna, heater control circuitry, or a transmitter or transceiver for wireless (e.g., Bluetooth) communication with a command center (shown and described below, with reference to FIG. 2) and/or other remote compute device (such as a mobile device of a user). The sensor(s) 114 can include one or more of: a pressure sensor, a temperature sensor, a position sensor, an orientation sensor, etc. The identifier(s) 123 can include any suitable data configured to identify the vaporizer 100A (e.g., a serial number, a barcode, a QR code, code stored in a memory, a chip identifier assigned to a tracking component of the vaporizer 100A and stored in a memory, and/or identification included in a signal transmitted by, for example, an RFID tag) and can be included in any component that is configured to store or represent an identity of the vaporizer (e.g., a near-field communication (NFC) device such as an RFID tag, a label including a barcode or a QR code, a tracking component including a code or signature stored in a memory (e.g., a digital signature based on a chip identifier assigned to a tracking component of the vaporizer), etc.) such that the vaporizer 100A may be identified and/or recognized by an external device (e.g., a fill station and/or a remote compute device). In some implementations, the identifier 123 is scanned or read one or more of: during (or upon completion of) manufacturing, during (or upon completion of) filling, or when in possession of a user (e.g., scanned by a mobile device of the user, for example using a camera thereof, via a software application stored thereon). The identifier can thus be used for one or more of registration, identification, or validation of the vaporizer (and/or a component thereof).

The processor 124 can include one or more of: a general purpose processor, a central processing unit (CPU), a microprocessor, a digital signal processor (DSP), a controller, a microcontroller, a state machine and so forth. Under some circumstances, a "processor" may refer to an application specific integrated circuit (ASIC), a programmable logic device (PLD), a field programmable gate array (FPGA), etc. The term "processor" may refer to a combination of processing devices, e.g., a combination of a DSP and a microprocessor, a plurality of microprocessors, one or more microprocessors in conjunction with a DSP core or any other such configuration.

The additive(s) 116 can include one or more flavorants. The membrane(s) 118 can be disposed on an outer surface of the vaporizer 100A (e.g., within an opening defined by the housing 101) and arranged such that carrier material and/or additive can be supplied to the reservoir 104 via the membrane(s) 118. The membrane(s) 118 can include a valved impermeable or semi-permeable material, for example comprising a rubber, polyvinyl chloride (PVC), etc. The indicator(s) 112 can include one or more of: an illumination source (e.g., one or more light-emitting diodes), a speaker, a display screen, a vibration component (e.g., a vibration motor or a piezoelectric vibrating element), etc.

In some embodiments, the disposable vaporizer 100A is configured such that, when a user sucks, or "draws," on the mouthpiece, the resulting change in pressure within the vaporizer 100A is measured by a sensor (e.g., a pressure sensor) of the sensor(s) 114. In response to the sensor 114 sensing a change in pressure (e.g., above a threshold change in pressure or to a threshold pressure level), the processor 124 can actuate the heater control circuitry of the electronics 122 to pass a current through the heating element that is in contact with, or in sufficiently close proximity to, the carrier material or a wick material containing at least a portion of the carrier material, so as to cause the volatilization of a portion of the carrier material. One or more characteristics of the current or affecting the delivery of the current passed through the heating element (e.g., voltage, wattage) can be controlled by the processor 124 based on, for example, an ambient temperature measured by a temperature sensor of the sensor(s) 114, a resistance of the heating element, and/or a heating profile or target temperature range associated with the carrier material (e.g., as determined by the processor 124 and/or provided to the processor 124 prior to use). The volatilized carrier material, or vapor, travels toward the mouthpiece via one or more of the expansion chamber(s) and one or more of the fluidic channels until it exits the vaporizer for inhalation by the user. In some embodiments, the disposable vaporizer 100A can be coupled to a mobile device (e.g., a mobile phone, tablet, or computer) via, for example, Bluetooth or Wifi, such that the mobile device can control one or more operations of the disposable vaporizer 100A. For example, the mobile device can lock and/or unlock the disposable vaporizer 100A such that the processor 124 does not actuate the heater control circuitry when locked and the processor 124 can actuate the heater control circuitry when unlocked. In some embodiments, the disposable vaporizer 100A will not operate to trigger heater control circuitry without approval from a mobile device associated with the disposable vaporizer 100A. For example, in some embodiments, each time a user attempts to actuate the disposable vaporizer 100A for heating and vaporization of carrier material (e.g., via applying suction to the mouthpiece or actuating a mechanical interface (e.g., button), the disposable vaporizer 100A can request approval for operation from the mobile device and/or a command center with which the disposable vaporizer 100A is associated. The disposable vaporizer 100A can then operate to heat and vaporize carrier material only if the disposable vaporizer 100A receives an unlock message from the mobile device and/or the command center. In some embodiments, the disposable vaporizer 100A will only require an initial unlock message upon initial coupling of the disposable vaporizer 100A with a mobile device. In some embodiments, the disposable vaporizer 100A and/or the mobile device can be configured to send an identifier 123 of the disposable vaporizer 100A to the command center to authenticate the disposable vaporizer 100A prior to the mobile device sending an unlock message to the disposable vaporizer 100A. In some embodiments, the command center can authenticate the identifier 123 by comparing the identifier 123 to a provenance record or database to determine whether the identifier 123 is associated with a particular source. In some embodiments, the command center can authenticate the identifier 123 by analyzing the identifier 123 to determine information (e.g., source information or fill data) about the disposable vaporizer 100A.

Figure 1B:
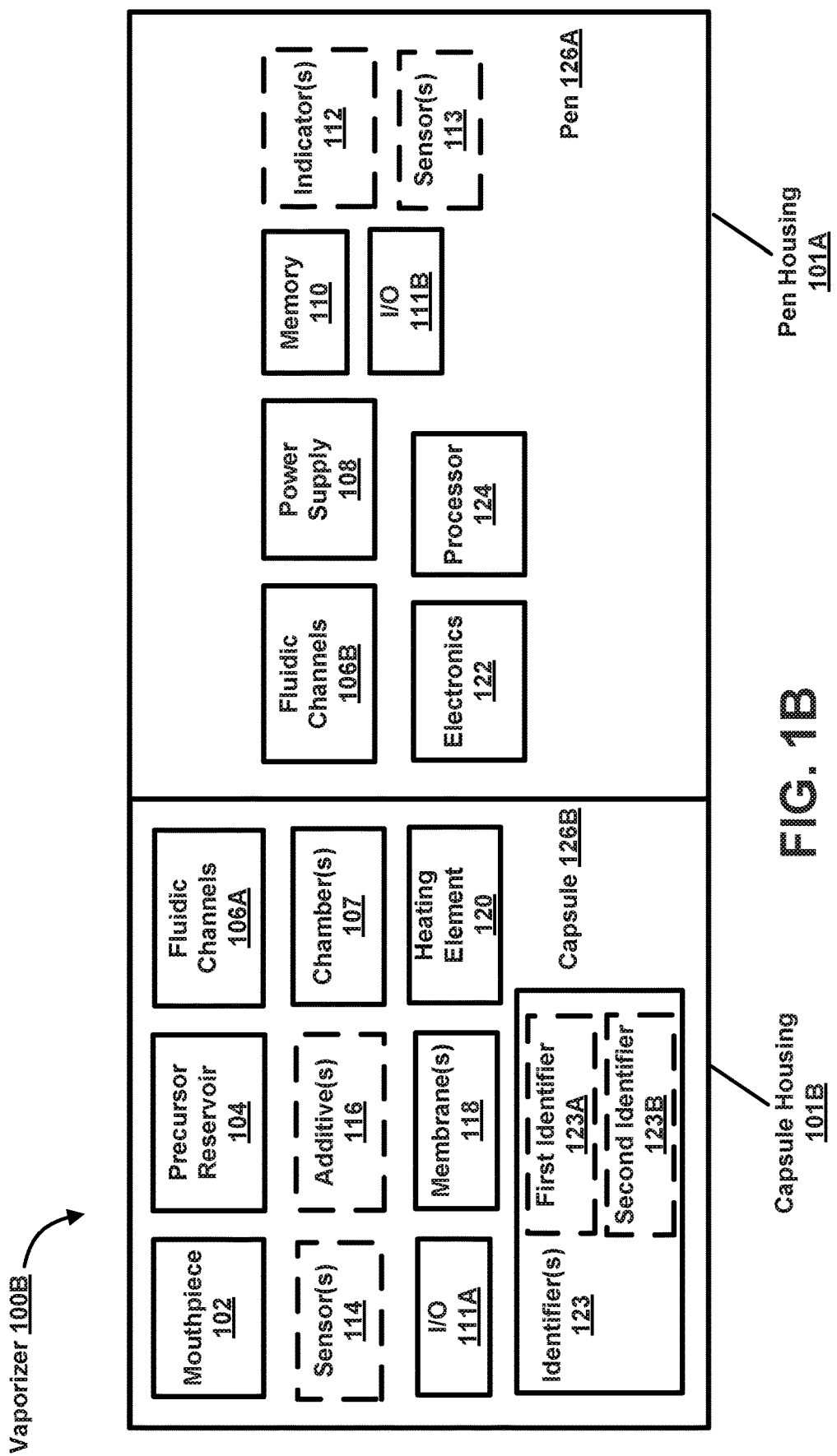
FIG. 1B is a schematic block diagram of a reusable vaporizer, according to an embodiment.

FIG. 1B is a schematic block diagram of a reusable vaporizer 100B, according to an embodiment. As shown in FIG. 1B, the reusable vaporizer 100B includes a pen portion 126A and a capsule portion 126B. The pen portion 126A and the capsule portion 126B of the reusable vaporizer 100B can collectively include components that are the same or similar in structure and/or function to the components of the vaporizer 100B described above. For example, the capsule portion 126B (also referred to as a "cartridge," a "capsule assembly," or a "capsule") includes a mouthpiece 102, a precursor reservoir 104, one or more fluidic channels 106A, one or more chambers 107, a heating element 120, membrane(s) 118, input/output module 111A, identifier(s) 123, optionally sensor(s) 114, and optionally additive(s) 116, all disposed within a capsule housing 101B. The pen portion 126A (also referred to as a "pen") includes fluidic channels 106B, a power supply 108, memory 110, input/output module 111B, electronics 122, a processor 124, an input/output module 111B, and optionally indicator(s) 112 and sensor(s) 113, all disposed within a pen housing 101A. The pen portion 126A can include an interface (e.g., including a portion of the electronics 112) configured to engage with the capsule 126A. The interface can include, for example, connectors (e.g., pogo pins) coupled to or included in a printed circuit board (that may be coupled to the processor 124, memory 110, and/or other electronics 122) and configured to engage with the capsule 126B such that the processor 124 can receive information contained in a memory of the capsule 126B. The pen portion 126A (i.e., the pen housing 101A and its contents) can also be referred to as a "battery portion" of the vaporizer 100B.

The capsule 126B can be manufactured, shipped and/or sold separately from the pen 126A, and assembled by a user to form the vaporizer 100B. To assemble the vaporizer 100B, a user may, prior to use (e.g., upon purchase of a new capsule), connect the capsule 126B with the pen portion 126A of the vaporizer 100B. The capsule 126B and the pen portion 126A can be configured to be mechanically and electrically connected, for example by one or more of screw attachment, press-fit attachment, snap-fit attachment, magnetic attachment, or any other suitable connection means. As can be inferred from the foregoing, the pen 126A can be considered the reusable portion of the vaporizer 100B, and the capsule 126B can be considered a disposable or "replaceable" portion of the vaporizer 100B.

The identifier(s) 123 can include any suitable data configured to identify the vaporizer 100A (e.g., a serial number, a barcode, a QR code, code stored in a memory, an identifier assigned to a chip (e.g., printed on the chip during manufacture) on which an authentication signature stored in a memory is based, and/or identification included in a signal transmitted by, for example, an RFID tag) and can be included in any component that is configured to store or represent an identity of the vaporizer (e.g., a label including a barcode or a QR code, a near-field communication (NFC) device such as an RFID tag, a tracking component including a code or an authentication signature stored in a memory, etc.) such that the vaporizer 100A may be identified and/or recognized by an external entity or device (e.g., a manufacturing station, a fill station, a mobile device, etc.) and/or the pen portion 126A. In some embodiments, the capsule 126B can include a first identifier 123A (also referred to as a first capsule identifier) and a second identifier 123B (also referred to as a second capsule identifier). The first identifier 123A can be configured to be read or scanned by, for example, a filling station configured to fill the reservoir 104 of the capsule 126B with carrier material. The second identifier 123B can be configured to be read or scanned by, for example, the processor 124 of the pen 126A. The first identifier 123A can be a visual identifier and/or an identifier placed on or associated with the packaging of the capsule 126B and the second identifier 123B can be an electronic identifier. The first identifier 123A can be, for example, a QR code or a barcode and can be displayed on a label affixed to an outer surface of the capsule 126B. The second identifier 123B can be, for example, an identifier assigned to the capsule (e.g., printed on the capsule) during manufacturing upon which an authentication signature written on a memory of the capsule 126B is based and can be included, for example, in a tracking component included within the capsule 126B and including a memory. Both the first identifier 123A and the second identifier 123B can be unique to the particular capsule 126B with which they are associated (i.e., each capsule 126B configured to couple to the pen 126A can have a distinct first identifier 123A and a second identifier 123B).

In some embodiments, the processor 124 of the pen 126A can be configured to be coupled to the tracking component of the capsule 126B upon an attachment of the capsule 126B to an interface of the pen portion 126A (e.g., via establishing a mechanical and electrical connection between the capsule 126B and the pen portion 126A) such that the processor 124 can be in electronic communication with a memory of the tracking component. The processor 124 can be configured to read information from and/or write information to the memory of the tracking component. The tracking component may be, for example, an integrated circuit (e.g., Application-Specific Integrated Circuits (ASICs)). The tracking component can include a memory and can be configured to contain data related to the capsule 126B. In some implementations, the tracking component 128 may contain capsule identification information corresponding to the capsule 126B such that the processor 124 can recognize the capsule 126B and such that information about the capsule 126B and/or the contents of the capsule 126B can be received from the tracking component 128 by the processor 124. For example, the processor 124 can read the second identifier 123B stored in the memory of the capsule 126B.

In some embodiments, the processor 124 can be configured to be loaded with a firmware during a manufacturing phase of the processor 124 such that the firmware can be programmatically used to perform authentication of the capsule 126B using one or more cryptographic methods. For example, in some implementations, the identifier 123 can include a digital signature (also referred to as an authentication signature) stored in the memory of the tracking component (e.g., a chip) of the capsule 126B that can be based on a private key. In some implementations, a digital signature stored in the memory of the tracking component can be based on a private key and on a unique identifier 123 (e.g, an unmodifiable unique identifier also referred to as a chip unique identification or chip unique ID) that is printed on the tracking component (e.g., during manufacturing of the tracking component). The firmware of the processor 124 can include use a public key associated with the private key and an authentication module and can be configured to access the digital signature and the unique identifier 123 of the tracking component and to use the public key to verify the digital signature written onto the tracking component of the capsule 126B to verify the authenticity of the capsule 126B and/or of a source of the capsule 126B. For example, the processor 124 can compare the signature stored in the memory of the tracking component and a public key (e.g., stored in the memory 110 of the pen 126A) with the chip unique ID. The processor 124 can then determine whether or not to authenticate the capsule 126B based on whether the signature and the public key is a match for the chip unique ID. Any suitable methods or algorithms of authentication can be used to verify the authenticity of the capsule 126B. For example, in some implementations, the vaporizer 100B can use Elliptic Curve Digital Signature Algorithm (ECDSA) methods to authenticate the capsule 126B and/or the pen 126A. In some implementations, if the pen 126A does not determine the capsule 126B to be authenticated, the pen 126A can reject the capsule 126B (e.g., disable or fail to initiate activation of heating control circuitry of the pen 126A and/or the capsule 126B such that carrier material in the capsule 126B is not vaporized).

In some implementations, the memory of the tracking component of the capsule 126B can be accessed and the second (e.g., electronic) identifier 123B read one or more of: during (or upon completion of) manufacturing, during (or upon completion of) filling, or when in possession of a user (e.g., upon engagement of the capsule 126B with the pen 126A). In some implementations, the first identifier 123A (e.g., a visual or NFC identifier) of the capsule 126B (e.g., a QR code affixed to an outer surface of the capsule 126B) can be scanned one or more of: during (or upon completion of) manufacturing, during (or upon completion of) filling, or when in possession of a user (e.g., scanned by a mobile device of the user, for example using a camera thereof, via a software application stored thereon). The second identifier 123B written and stored in the memory of the tracking component and the first identifier 123A (e.g., an identifier 123 affixed to an outer surface of the capsule 126B) can thus be used individually or collectively for one or more of registration, identification, or validation of the vaporizer 100B (and/or a component thereof such as the capsule 126B).

In some embodiments, the memory included in the tracking component 128 of the capsule 126B can be configured, for example at an initial manufacturing phase or at a filling phase, such that an identifier 123 (e.g., a unique identifier assigned to the capsule 126B upon which an authentication signature may be based) and/or an authentication signature can be written in the memory. For example, a manufacturing station can write a distinct second identifier 123B (e.g., a unique identifier assigned to the capsule 126B) and/or a digital signature onto the memory of the tracking component of each capsule 126B produced by the manufacturing station, the digital signature based on a unique identifier printed on the tracking component and a private key stored in the manufacturing station. In some embodiments, each capsule 126B has a different authentication signature written onto its memory compared to all of the other capsules 126B produced by the manufacturing station (e.g., based, at least in part, on the unique identifier assigned to the tracking component of each individual capsule during manufacturing). Additionally, the manufacturing station or another manufacturing station can apply a first identifier 123A to the capsule 126B via, for example, affixing a label including a QR code or a bar code or installing an RFID chip into the capsule 126B. The second identifier 123B (e.g., the unique identifier assigned to the capsule 126B upon which the authentication signature may be based) and the first identifier 123A (e.g., a QR code affixed to an outer surface of the capsule 126B) can be associated with each other, for example, by being transmitted to a remote command center and stored in a memory of the command center. Thus, each capsule 126B can be registered in the memory of the command center by storing the first identifier 123A and the second identifier 123B of each respective capsule.

In some instances, a filler station can receive the capsule 126B and read the first identifier 123A. For example, the filler station can scan a QR code affixed to an outer surface of the capsule 126B before, during, or after filling the reservoir 104 of the capsule 126B. In some implementations, the filler station can then send information to be associated with the capsule 126B (e.g., information related to the carrier added to the reservoir 104) to the command center to be associated with the first identifier 123A (the QR code). In some implementations, the filler station can fill the capsule 126B according to instructions provided by the command center based on the first identifier 123A the filler station sends to the command center. The command center can associate the information associated with the capsule with the first identifier 123A and/or the second identifier 123B (which may have been provided to the command center during or after manufacturing of the capsule 126B). The command center can store the information (e.g., fill information) in a provenance record or database.

In some embodiments, a filler station can receive the capsule 126B, access the memory included in the capsule 126B, and read the identifier 123 stored in the memory included in the capsule 126B. For example, the memory included in the capsule 126B can be accessed by a filler station (also referred to as "fill station" or "filling station" herein) at a filling phase, as described in further detail herein. In some instances, the fill station can read the identifier 123 stored in the memory included in the capsule 126B and use the identifier 123 to verify the identity and/or authenticity of the capsule 126B and to associate the capsule 126B with particular fill data (e.g., received from a command center in response to the fill station requesting fill data associated with the capsule 126B and/or the identifier 123). In some instances, the filler station can fill the capsule 126B with an appropriate carrier based on the fill data. In some embodiments, upon fill completion, the filler station can access the memory included in the capsule 126B and write an identifier (e.g., a carrier identifier) associated with the fill data received from the command center and/or used to fill the reservoir 104 of the capsule 126B (e.g., carrier material, batch of filling, etc.) on the memory. In some implementations, the capsule identifier 123 can be associated with the fill data and/or the carrier identifier by the fill station and/or the command center. In some implementations, the fill station can write and store the fill data and/or the carrier identifier in the memory included in the capsule 126B after completion of filling. In some instances, the writing of the fill data and/or the carrier identifier in the memory included in the capsule 126B can be performed prior to the filling or during the filling of the capsule 126B.

Figure 2:
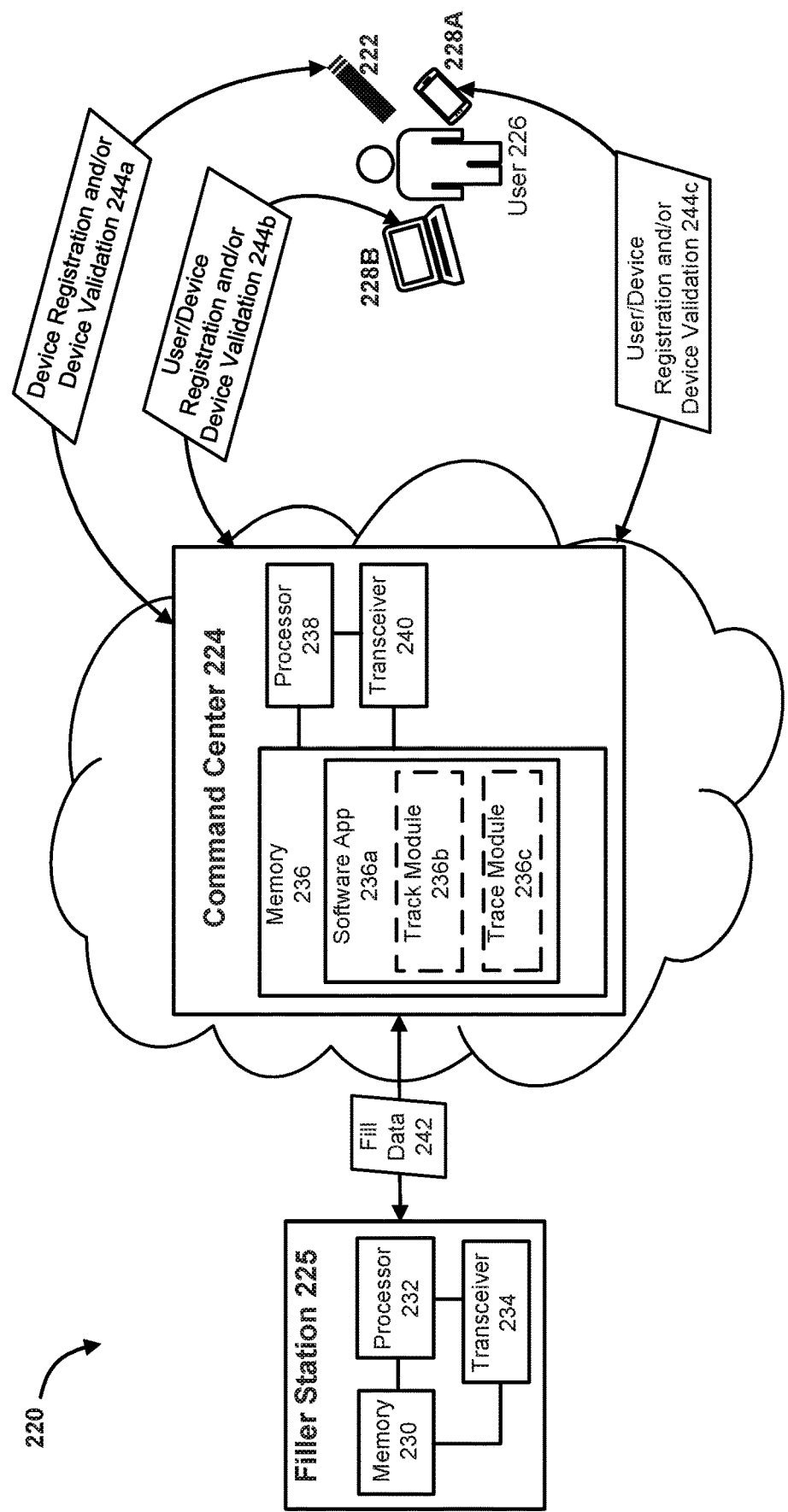
FIG. 2 is an illustration of a system for managing vaporizer security and/or traceability, in accordance with some embodiments.

FIG. 2 is an illustration of a system for managing vaporizer security and/or traceability, in accordance with some embodiments. As shown in FIG. 2, the system 220 includes a command center 224 (e.g., a cloud-based server, a centralized server and/or the like) in wireless network communication with a filler station 225, a vaporizer 222 of a user 226, and a mobile device 228A and/or a compute device 228B (e.g., a laptop or desktop computer) of the user 226. The filler station 225 includes a memory 230 operably coupled to a processor 232. The memory 230 can store data (e.g., in the form of a database table storing data records) associated with one or more of: carrier formulations, carrier provenance, capsule compatibility, capsules that have been filled at the filler station 225 (e.g., capsule identifier(s)), filler station maintenance history, filler station maintenance schedules, and fill settings such as carrier dispense pressure, carrier dispense temperature, carrier dispense duration, carrier dispense volume, etc. The filler station 225 also includes a transceiver 234 operably coupled to the processor 232 and the memory 230. The transceiver 234 facilitates communications between the filler station 225 and the command center 224. For example, the filler station 225 may send fill data 242 to the command center 224. Example fill data include, but are not limited to, identifiers of one or more of: capsule type, capsule capacity, carrier type, carrier amount, carrier origin/provenance, carrier constituent concentration (s), fill date/time stamp, fill conditions, etc.

In some embodiments, the filler station 225 can be configured to read and/or write to a memory included in a capsule, as described previously. In some implementations, the filler station 225 can read an unfilled capsule identifier (e.g., an authentication code or signature) stored in a memory included in an unfilled capsule. In some implementations, the filler station 225 can fill each capsule with a specific carrier material, access a memory included in that capsule that is filled with the specific carrier material, and, upon fill completion, write a carrier identifier associated with the specific carrier material that was filled in that capsule, thus marking the filled capsule with data related to the carrier included in the filled capsule (e.g., carrier formulations, carrier provenance, capsule compatibility, etc.). This marking can be used to verify authenticity of a capsule before use as described herein. In some implementations, the filler station can register the capsule and store an association between an identifier of the carrier material being filled and the identifier of the capsule. In some implementations, authentication of a capsule using a stored key or cryptographic signature can serve as a primary method of verification and registration of a capsule after filling with a carrier material can serve as a second method of verification of a capsule. In some implementations, the authentication and/or registration of a capsule can be verified when the capsule is inserted into or coupled to a pen of a vaporizer. In some implementations, the authentication and/or registration of the capsule can be verified at each insertion of the capsule. In some implementations, the authentication and/or registration of the capsule can be verified at each use of the capsule for inhalation of volatilized substances. In some implementations, the authentication and/or registration of the capsule can be verified at each connection of the vaporizer with the command center 224 and/or a compute device 228A or 228B. The command center 224 includes a memory 236 operably coupled to a processor 238, and a transceiver 240 configured to facilitate wireless network communications with the filler station 225, the vaporizer 222 of a user, and the mobile device 228A and/or compute device 228B of the user. For example, messages related to vapor device registration and/or vapor device validation 244*a* can be exchanged between the command center 224 and the vaporizer 222. Alternatively or in addition, messages related to user registration, vapor device registration and/or vapor device validation 244*b* can be exchanged between the command center 224 and the compute device 228B of the user. Alternatively or in addition, messages related to user registration, vapor device registration and/or vapor device validation 244*b* can be exchanged between the command center 224 and the mobile device 228A of the user.

The memory 236 stores a software application ("app") 236*a*. In some implementations, an administrator of the command center 224 interacts with the software app 236 via an administrator view of the app, rendered via a graphical user interface (GUI) of a compute device in wireless or wired network communication therewith, and a user interacts with the software app 236 via a user view of the app, rendered via a graphical user interface (GUI) of a compute device of the user in wireless network communication with the command center 224. The app 236*a* can include one or more software modules, such as a track module 236*b* and/or a trace module 236*c*.

The track module 236*b* can include instructions to cause the processor 238 to obtain contemporaneous (e.g., real-time or substantially real-time) location information for one or more vaporizer components (e.g., capsules or vaporizer pens, such as capsule 126B and pen 126A, respectively, of FIG. 1B), the vaporizer 222, and/or one or more compute devices (e.g., the mobile device 228A or the compute device 228) of a user of the vaporizer 222. Such location can be obtained, for example, by querying one or more of the aforementioned devices (e.g., via one or more associated onboard location sensors of the device(s), such as a global positioning sensor (GPS) receiver). The track module 236*b* can also include instructions to cause the processor 238 to store the location information and, optionally, transmit the location information to one or more requestors of the wireless network (e.g., requestors associated with remote compute devices such as mobile device 228A or a third party).

For example, some substances (e.g., controlled substances) that may be included in one or more carrier materials and consumable via the vaporizer 222 may be lawfully consumed in certain geographical locations whereas consumption of the substances may not legally be permitted in other geographical locations. The track module 236b can receive contemporaneous location information associated with a capsule and/or the vaporizer 222 identified to include a specific carrier material including a known controlled substance. In some implementations, the track module 236b can have access to information regarding location-based permissions and/or restrictions with respect to the consumption of specific substances. Based on the location-based restriction information, the location of the capsule or vaporizer 222, and information regarding the constituent substances included in the carrier material in the capsule or vaporizer 222, the track module 236b can determine whether operation of the vaporizer 222 to volatilize the carrier material in the capsule will be permitted. The processor 238 can then send instructions to the vaporizer 222 and/or the compute device 228A or 228B via the transceiver 240 based on the determination. For example, the instructions can permit the use of the vaporizer 222 by validation of the user and/or vaporizer 222, or can block or disable the use of the vaporizer 222 by not validating the user and/or vaporizer 222.

In some implementations, a validation of a user and/or the vaporizer 222 may be conducted at each use of the vaporizer 222 to consume substances (i.e., each instance of use where a user draws air and/or aerosols through the mouthpiece of a vaporizer). In some implementations, a validation of the user 226 and/or vaporizer 222 can be conducted each time a user 226 (e.g., via the compute device 228A or 228B) and/or vaporizer 222 connects to the command center 224, a user 226 interacts with a software application associated with the vaporizer 222, and/or at predetermined intervals. In some instances, the track module 236b can receive updated information regarding the location of the vaporizer 222 including the controlled substance, and based on the updated location information, the track module 236b can update instructions related to permissions of usage. For example, based on updated location information the track module 236b can unblock the use of a blocked vaporizer 222 by validating the user 226 and/or the vaporizer 222.

The trace module 236c can include instructions to cause the processor 238 to request, store and/or transmit historical data associated with the manufacture and movement (e.g., within the supply chain), of one or more vaporizer components (e.g., capsules or vaporizer pens, such as capsule 126B and pen 126A, respectively, of FIG. 1B), the vaporizer 222, and/or one or more compute devices (e.g., the mobile device 228A or the compute device 228) of the user 226 of the vaporizer 222. In other words, the trace module 236c (optionally in combination with the track module 236b) monitors the chain-of-custody of one or more vaporizers to ensure their safety and authenticity. The historical data can include one or more of: carrier ingredients, carrier formulation, nicotine concentration, nicotine plant genetics, nicotine provenance data (e.g., the tobacco plant(s) from which the nicotine was derived, the grow location of the nicotine plant(s), the grow and/or harvesting date of the nicotine plant(s), etc.) cannabinoid concentration(s), cannabinoid provenance data (e.g., the *cannabis* plant(s) from which the cannabinoid(s) were derived, the grow location of the *cannabis* plant(s), seed information associated with the *cannabis* plant(s), the date on which the *cannabis* seeds were planted, the grow and/or harvesting date of the *cannabis* plant(s), the dispensary from which the cannabinoid(s) were obtained, etc.), active ingredient (e.g., drug) concentration, extraction method(s) (and details thereof) used when converting the *cannabis* plant(s) into carrier material, inactive ingredient concentration, functionality of the vaporizer (e.g., physics of vapor generation, sequence of steps performed by the vaporizer when activated, etc.), details regarding effects within/on the user when the vapor is inhaled, and/or the like. In some implementations, the historical data (or a subset thereof) is rendered via a graphical user interface (GUI) for presentation to a user, e.g., via a software application running on a mobile compute device of the user and/or running on a laptop or desktop computer of the user.

In some implementations, the trace module 236c can be configured to generate and maintain a list or database of capsules (e.g., capsule 126B described above with respect to FIG. 1B) that can be used with a vaporizer (e.g. with a pen 126A of a vaporizer 110B as described above with respect to FIG. 1B). In some implementations, the trace module 236c can (optionally in combination with the track module 236b) maintain a list or database of capsules that were authenticated at or after filling (e.g., by a filler station) and a list of capsule identifiers associated with the authenticated capsules. In some implementations, the trace module 236c can maintain a list or database of first (e.g., visual or NFC) identifiers associated with second, electronic identifiers, such that each capsule can be identified via one of the first or second identifiers. In some implementations, the trace module 236c can maintain a list or database of disposable vaporizers (similar to or the same as the disposable vaporizer 100A) that can be authenticated and authorized for use (e.g., unlocked by a mobile device) (e.g., by verifying an identifier of the vaporizer corresponds to an identifier stored in the memory of the command center 224).

In some implementations, at any point in time a set of capsules and/or carrier material disposed in the set of capsules can be identified as being faulty or can undergo a regulatory restriction of use (e.g., restriction of use in a specific region or by a specific user group based on, for example, age). The trace module 236c can be used to generate a recall list or a block list including capsule identifiers associated with each of the capsules in the set. In some embodiments, the trace module 236c can associate a recall identifier with a specific capsule identifier or carrier identifier. When an incoming request for verification or validation of a capsule is received by the command center 224 (e.g., a capsule attach event detection message including a capsule identifier), the trace module 236c can be configured to determine whether the identifier of the capsule is on the recall list or has been associated with a recall flag or indication. If the identifier is determined to be on the recall list, the trace module 236c can block the verification of the capsule associated with the recall. Thus, in some embodiments, in case of a recall associated with one batch of capsules for example, the system described herein can be used to block a capsule from being validated at a first instance of engagement with a vaporizer pen or from being further validated at a time point following the recall being issued, even if the capsule was previously validated before the identifier of the capsule was place on the recall list.

In some instances, the trace module 236c can receive a request for user verification and based on a determination of a user characteristic (e.g., an age of a user), the trace module 236c can block the verification of the user for a specific capsule associated with an identifier (e.g., a carrier identifier associated with a substance that is associated with a regulatory ban of use by a specific group of users and/or in a specific geographical location). For example, the user validation or verification can include uploading an image of a government-issued identification card for review by the control center 224. The control center 224 can determine the age of the user 226 based on the image. In some implementations, the trace module 236c can be configured to implement a substance block for a particular user based on the user verification such that particular substances (e.g., associated with particular carrier identifiers) can be validated for use by the user and other substances cannot be validated (e.g., based on regulatory age restrictions).

In some implementations, the trace module 236c and/or the track module 236b can be configured to send instructions to write a status update to a memory included in a capsule. For example, the trace module 236c and/or the track module 236b can receive information related to a recall status of a batch of capsules associated with a set of identifiers. Based on the information, the system can be configured such that the command center (e.g., command center 224) can send instructions to a vaporizer (e.g., vaporizer 222) to write the recall status (e.g., write a recall identifier) to the memory included in the capsule used with the vaporizer. When the recall status is written in the memory of the capsule, the vaporizer may reject the capsule for that particular use and for any subsequent attachment of the capsule to the vaporizer. Furthermore, the written recall status in the memory of the capsule can be configured to be read by any vaporizer that the capsule is subsequently attached to such that the capsule is rejected from any other vaporizer. While not shown in FIG. 2, the system can include one or more manufacturing stations or manufacturing jigs that are configured to manufacture empty/unfilled capsules. The manufacturing station can be configured to store an identifier (e.g., write a digital signature using a private key based on the identifier) in a memory included in each capsule and/or place an identifier (e.g., a QR code, bar code) on an external surface of each capsule for registration, verification and/or validation at various steps downstream in the process of making and using the capsule.

The terms "instructions" and "code" should be interpreted broadly to include any type of computer-readable statement(s). For example, the terms "instructions" and "code" may refer to one or more programs, routines, subroutines, functions, procedures, etc. "Instructions" and "code" may comprise a single computer-readable statement or many computer-readable statements.

Figure 3A:
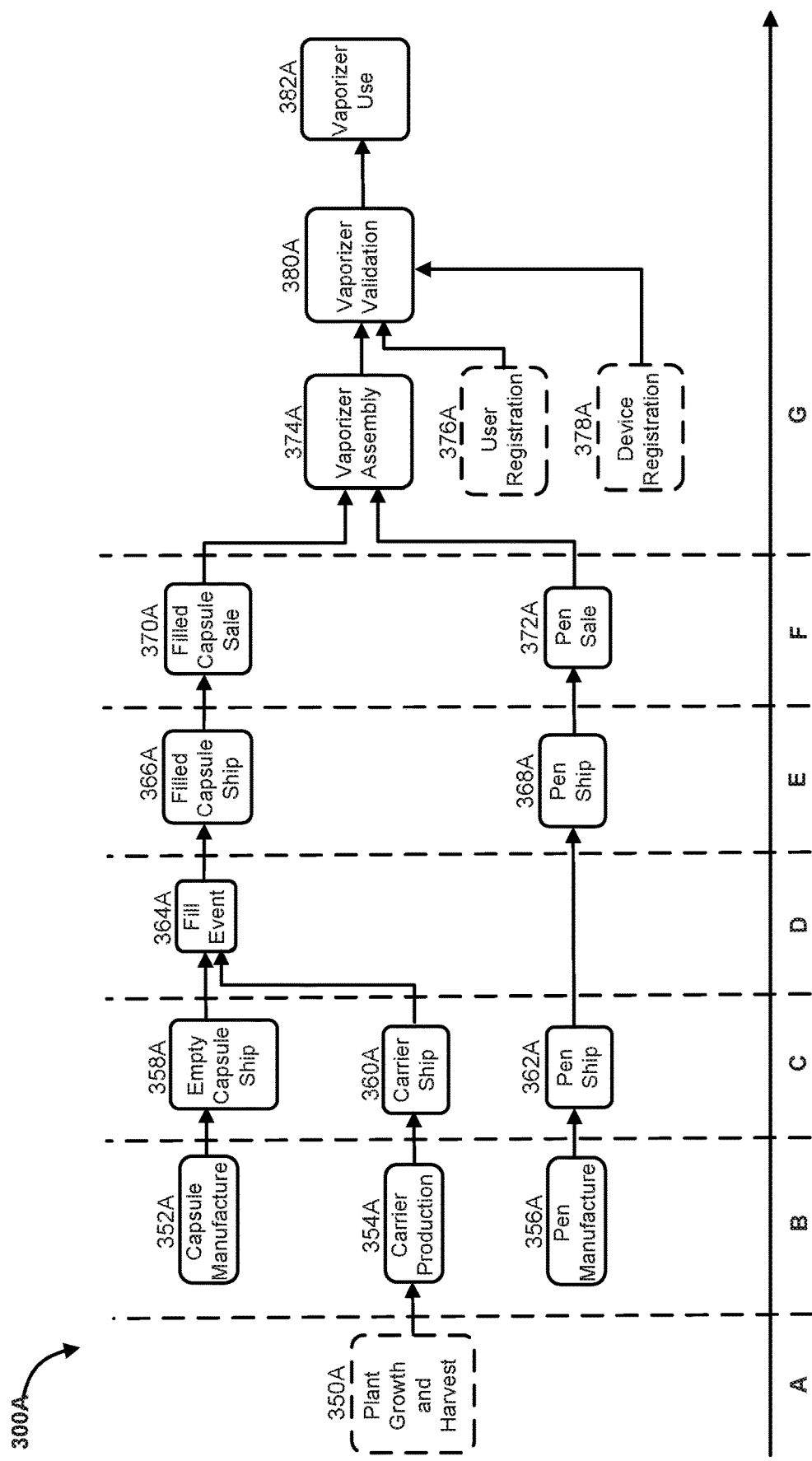
FIG. 3A is a flow diagram of a vaporizer supply chain, according to an embodiment.

FIG. 3A is a flow diagram of a vaporizer supply chain, according to an embodiment. As shown in FIG. 3A, the supply chain 300A includes a sequence of phases (labelled "A" through "G" in FIG. 3A). An initial, optional, phase related to the growth and harvesting of plant mater (350A, phase A), such as tobacco or *cannabis*, for subsequent incorporation into a vaporizer. During an initial manufacturing phase (phase "B"), unfilled/empty capsules (such as capsule 126B in FIG. 1B) are manufactured at 352A, carrier materials (e.g., incorporating one or more parts or extracts of the plant matter harvested at 350A) are produced at 354A, and vaporizer pens (such as pen 126A in FIG. 1B) are manufactured at 356A. In some implementations, during or after the manufacturing of the unfilled/empty capsules, one or more identifiers can be included in or on the capsules. For example, a first identifier (e.g., a label including a QR code) can be affixed to an outer surface of each capsule. A second identifier can be written onto a memory of a tracking component included in the capsule. In some implementations, the second identifier can include a unique identifier assigned to the capsule upon which a digital signature can be based (e.g., generated using a private key) that can later be used to authenticate the capsule and/or verify authenticity of a source of the capsule using a suitable authentication algorithm. In some implementations, empty capsules can include a memory that can have a digital signature written into the memory at the manufacturing phase at 352A.

During phase "C," the manufactured empty capsules, carrier materials, and pens are shipped to appropriate locations for the next step (at 358A, 360A and 362A, respectively). For example, the empty capsules and the carrier materials are shipped to a location including a filler station, and the vaporizer pens may be shipped to a vendor, a distributor, and/or a user.

During phase "D," the empty capsules are filled (e.g., at a filler station such as the filler station 225 of FIG. 2) with carrier material at 364A. In some implementations, the filler station can read the first identifier associated with each capsule (e.g., an identifier such as a QR code or a bar code attached to a capsule). For example, a filler station can use a QR code reader to read a label attached to a capsule. The filler station can verify the authenticity of the unfilled empty capsule (e.g., verify a source of the empty capsule) using the capsule identifier (e.g., by querying a command center), obtain fill data associated with that capsule (e.g., from a remote command center), and/or fill the capsule with an appropriate carrier material according to the fill data. In some embodiments, the filler station can read the capsule identifier (e.g., QR code), fill the capsule with a carrier material, and then send the capsule identifier and fill data related to the carrier material (e.g., a carrier identifier) to a command center to be stored in a database.

In some embodiments, the filler station can read an identifier stored in a memory of a tracking component included in the capsule. For example, the filler station can include a chip reader configured to access the memory of the tracking component to read an authentication signature stored in the memory (e.g., the authentication signature based on an assigned identifier of the chip and/or capsule). In some implementations, the filler station can write in the memory included in each capsule an identifier that can be used to verify the authenticity of the capsule and/or identify the carrier material being filled in the capsule. For example, in some instances, the filler station can write a cryptographic digital signature in the memory included in each capsule filled such that a pen portion of a vaporizer can verify the cryptographic signature to authenticate the capsule downstream. In some instances, the writing the signature to the memory included in the capsule can be alternatively done at the manufacturing phase B of the capsule at 352A (e.g., by a manufacturing station or manufacturing jig). In some implementations, the filler station can write into memory an identifier that can be used to identify the carrier material and/or contents of the capsule. For example, the filler station can write a carrier identifier that provides information about the batch of each carrier material filled in each capsule (e.g., a dated numbered batch of tetrahydrocannabinol (THC) filled in a given period). In some instances, the filler station can generate an identifier that can be attached to a capsule packaging in the form of a label (e.g., a QR code, barcode, etc., attached to a capsule housing).

In some implementations, after the capsule is filled, the carrier material within the reservoir of the capsule can be tested and analyzed to determine its constituents and the resulting information (e.g., in the form of a Certificate of Analysis) can be associated to the capsule. The information may include particular data required by the law of one or more jurisdictions in which the capsule is intended or likely to be used. For example, the information can be added to a label (e.g., a label including an identifier such as a QR code) affixed to the outer surface of the capsule (e.g., by a filler station). The information can also be associated with the specific capsule in the memory of the command center (such as command center 224 described with respect to FIG. 2) such that the information can be accessed by a remote compute device and/or a mobile device (e.g., a mobile device associated with a vaporizer pen coupled to the capsule at a later time). In some instances, the information can be written on the memory of the capsule (e.g., by the filler station).

In some implementations, following filling of a capsule with carrier material and testing the carrier material in a capsule, the filler station can register the capsule by sending data to the command center including the identifier used by the filler station to identify the capsule (e.g., a QR code affixed to the capsule) and fill data (e.g., the identity of the carrier material filled in the capsule) such that the command center stores the association of the fill data and the identifier in a memory of the command center and associates the fill data with an assigned identifier (e.g., upon which an authentication signature was previously based) previously stored in the memory 236 (e.g., after being received by a manufacturer of the capsule). Thus, after being produced, filled, and tested, each capsule and characteristics of each capsule and/or carrier material disposed in the reservoir of each capsule can be registered into a tracking system (e.g., track module 236b), generating a database of each capsule produced and their respective characteristics. For example, the filler station can perform registration of each capsule by authenticating a capsule (using the digital signature stored in a capsule and/or by using the identifier attached to the capsule) and associating the identifier attached to the capsule (e.g., QR code) with the identifier (e.g., assigned to a chip or tracking component of the capsule at manufacture) associated with the digital signature stored on a memory of the capsule and/or with the identifier associated with the carrier material filled in the capsule. In some instances, the associating of the identifier attached to the capsule and identifier associated with the digital signature stored on a memory of the capsule (e.g., an assigned identifier used with a private key to generate the digital signature) and/or with the carrier identifier can alternatively be performed at the manufacturing phase B of the capsule at 352A (e.g., by a manufacturing station or manufacturing jig).

In some instances, the identifiers included on a label and/or written into a memory of capsules can be stored in a memory associated with a command center and used for registration, authentication, validation, and/or any other form of verification of a capsule before and/or during use). For example, as described previously, the list or database of capsules can be modified and/or updated based on any suitable information such that a first set of capsules are continued to be verified and allowed for use while a second set can be black listed or recalled (e.g., a batch of capsules recalled due to being identified as faulty or inauthentic) such that any request for verification of a capsule associated with a black listed or recalled identifier from a vaporizer associated with that capsule will be denied verification. In some instances, the vaporizer may be blocked from use with that capsule.

The filled capsules are then shipped, at 366A during phase "E," as are the pens (unmodified from phase "B"), for example to one or more retailers, distributors, and/or consumers. The filled capsules and the pens are then sold, at 370A and 372A, respectively, during phase "F." In some implementations, the sale of the filled capsules and/or the pens can occur prior to shipment in phase "E".

Once a user has purchased and/or otherwise obtained a capsule and a pen (e.g., sold separately or combined in a single package), the user can assemble them (e.g., via attaching the capsule to the pen) to form a vaporizer (at 374A, phase "G"). Optionally, a user registration 376A and/or a device registration 378A also occurs during phase "G." In some embodiments, the user registration 376A and/or device registration 378A can be triggered by a user input made, for example, via a software application such as software app 236a of FIG. 2. Alternatively or in addition, the user registration 376A and/or device registration 378A can be triggered by a "handshake" message exchange that automatically occurs (e.g., upon proximity detection) between the vaporizer and a compute device of the user, resulting in the presentation of input prompts to the user via the software application. Once the vaporizer assembly 374A (and, optionally, the user registration 376A and/or the device registration 378A) has been completed, a vaporizer validation 380A is performed (also during phase "G").

In some implementations, the newly-assembled vaporizer is configured to prevent vapor generation until the validation step 380A is successfully completed. In other implementations, the newly-assembled vaporizer is configured to function for a predetermined number of inhalations (or "draws"), and once the predetermined number of inhalations have taken place, the vaporizer automatically locks itself until the validation step 380A is successfully completed. As with the optional user and device registration processes 376A and 378A, the vaporizer validation can be triggered by a user input made, for example, via the software application running on the user's compute device (e.g., smartphone). Alternatively or in addition, the validation step 380A can be triggered by a "handshake" message exchange that automatically occurs (e.g., upon proximity detection) between the vaporizer and a compute device of the user, resulting in the presentation of input prompts to the user via the software application on his/her compute device. Alternatively or in addition, the validation step 380A can be triggered by a "handshake" message exchange that automatically occurs (e.g., upon proximity detection) between the vaporizer and a compute device of the user upon vaporizer assembly (i.e., attachment of the capsule to the pen), resulting in the automatic transmission of a validation request message (also referred to as a "capsule attach event detection message") to a remote server (e.g., a command center, such as the command center 224 of FIG. 2). However triggered, if the validation at the remote server is successful, an unlock message is sent from the remote server and received at one or both of the vaporizer and the user compute device, causing the vaporizer to be unlocked for use. If, however, the validation at the remote server is not successful, an alert message is sent from the remote server and received at one or both of the vaporizer and the user compute device, for example causing a visual, haptic, or audio indication that the vaporizer cannot be used. The validation can be based on one or more of the following non-exhaustive list of factors: capsule identifier, vaporizer identifier, user identifier, age of the user, user registration status, device registration status, recall flag setting, etc. Once the validation is successful, the user proceeds to use the vaporizer (382A). For example, a vaporizer identifier associated with a particular vaporizer or group of vaporizers can be stored in a memory of the vaporizer or otherwise included in or on the vaporizer similarly as described above with respect to the capsule identifiers. The user compute device can receive the vaporizer identifier from the vaporizer (e.g., via a transmitter of the vaporizer or scanning a label on the vaporizer) and can sent the vaporizer identifier to the remote server for validation. The remote server can compare the vaporizer identifier to a list or database and determine whether the vaporizer identifier is valid by determining whether the vaporizer identifier corresponds to a vaporizer identifier in the list. The remote server can also determine the validity of the vaporizer identifier based, at least in part, on whether any blocks or recalls have been associated with the vaporizer identifier and stored in the remove server.

In some implementations, the vaporizer validation at 380A can be performed at each engagement of a capsule and a pen (e.g., an insertion of the capsule into the pen) of the vaporizer. In some implementations, each time a new capsule is to be used with a vaporizer (e.g., each time an app associated with the vaporizer is opened on a mobile device of the user), the vaporizer validation at 380A can include authenticating the capsule, verifying the registration of the capsule, and/or verifying the registration of the device and/or the user. For example, the capsule can be authenticated by a firmware in the vaporizer reading and recognizing a cryptographic digital signature (e.g., generated based on an identifier assigned to the capsule in combination with a private key) stored in a capsule and/or an identifier (e.g., a QR code, barcode) associated with the capsule. In some instances, the authentication can be performed locally by the vaporizer. In some instances, the authentication can invoke one or more processes performed by a remote device such as a command center and/or a compute device. The registration of the capsule can be verified using one or more identifiers associated with the capsule. The user and/or device registration can be verified using identifiers associated with the user and/or device upon connection of a capsule to the pen. In some implementations, the vaporizer validation 380A can include a user validation step that includes validating details related to a user of a vaporizer (e.g., an age, personal identification, medical status, group affiliation, or other status of the user). In some implementations, the verification and/or validation of a capsule may be performed not only at each insertion of the capsule but also intermittently during use (e.g., each connection with a compute device, each use for inhalation of substances, and/or at predetermined intervals).

In some implementations, a vaporizer can implement a substance lock such that only certain substances may be used with that vaporizer. In some embodiments, a substance lock may be initiated by a user via an app in a compute device associated with the vaporizer via registration. The substance lock can be associated, for example, with a particular carrier identifier, user identifier, and/or capsule identifier. When a substance lock has been initiated (e.g., locking out a particular substance such as THC), upon insertion of a capsule including the locked out substance, the vaporizer can be configured to recognize the capsule as containing the locked out substance—for example via reading the identifier associated with the capsule packaging (e.g., a QR code) or an identifier stored in the memory of the capsule (e.g., an identifier assigned to the capsule that may have been used to generate a digital signature in combination with a private key). The vaporizer can then be configured to block use of the capsule for the duration of the substance lock. For example, upon receiving a capsule attach event detection message including a carrier identifier and a user identifier from a vaporizer, a compute device associated with the vaporizer can check for a substance lock associated with the carrier identifier and/or user identifier (e.g., via requesting information from a command center). If the command center determines that the capsule and/or carrier material within the capsule is not associated with a substance lock, the command center can send an unlock message to the mobile device and/or the vaporizer such that the vaporizer can operate. If the command center determines that the capsule and/or carrier material within the capsule is associated with a substance lock, the command center can send an alert to the mobile device and/or the vaporizer (and the vaporizer can be configured not to operate in the absence of an unlock message being sent to the mobile device and/or the vaporizer). In some implementations, the vaporizer can be configured to indicate to the user (e.g., via an indicator on the vaporizer or via an app executed on a compute device coupled to the vaporizer) that the inserted capsule contains a blocked substance and therefore is blocked from use. In some implementations, the substance lock can be a partial lock, limiting the consumption of a particular carrier material to a particular dose or amount or a particular dose or amount per a particular time period (e.g., a day, week, or month). In some implementations, such a limitation can be written directly on a chip (e.g., the tracking component) of the capsule by the vaporizer (e.g., after receiving such an instruction from a mobile device). In some implementations, in response to receiving a capsule identifier and/or carrier identifier, a remote device or server can send instructions associated with the particular capsule or carrier to the vaporizer or the remove device, respectively, such that the vaporizer operates according to the instructions. For example, the instructions can include a particular current to be applied to a heating element of the vaporizer or capsule, a resistance of the heating element, and/or a heating profile or target temperature range according to which the heating element is to be heated.

Figure 3B:
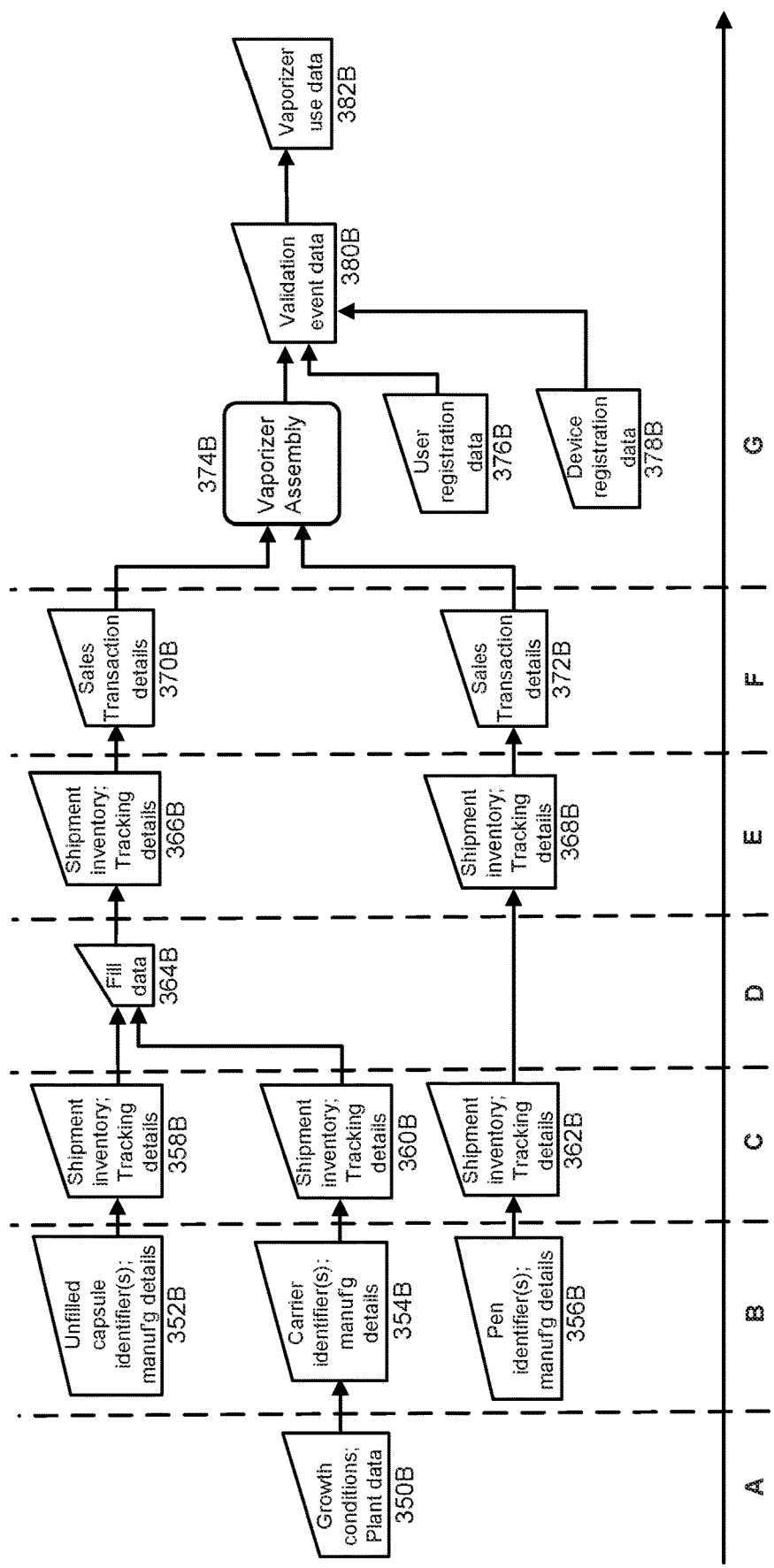
FIG. 3B is a diagram showing example data collected by a command center during various events of the vaporizer supply chain of FIG. 3A.

FIG. 3B is a diagram showing example data collected, e.g., by a command center (such as the command center 224 of FIG. 2) or other centralized server, during each of the various events of the vaporizer supply chain of FIG. 3A. The numerical portions of the reference numerals of FIG. 3B correspond to the numerical portions of the reference numerals of FIG. 3A. More specifically, at the plant growth and harvesting step 350A of FIG. 3A, data such as growth conditions and plant data, 350B in FIG. 3B, can be sent to/collected by the command center. At the capsule manufacture step 352A of FIG. 3A, data such as unfilled capsule identifier(s) and manufacturing details, 352B in FIG. 3B, can be sent to/collected by the command center. In some implementations, a private key can be stored in a memory of a manufacturing station configured to produce a capsule such that the private key can be used to generate a cryptographic signature stored in the capsule such that the capsule can be authenticated using the signature by another device having access to the public key associated with the private key. At the carrier production step 354A of FIG. 3A, data such as carrier identifier(s) and manufacturing details, (354B) in FIG. 3B, can be sent to/collected by the command center. At the pen manufacture step 356A of FIG. 3A, data such as pen identifier(s) and manufacturing details, (356B) in FIG. 3B, can be sent to/collected by the command center. At the empty capsule ship step 358A of FIG. 3A, data such as shipment inventory data and shipment tracking details, (358B) in FIG. 3B, can be sent to/collected by the command center. At the carrier ship step 360A of FIG. 3A, data such as shipment inventory data and shipment tracking details, (360B) in FIG. 3B, can be sent to/collected by the command center. At the pen ship step 362A of FIG. 3A, data such as shipment inventory data and shipment tracking details, (362B) in FIG. 3B, can be sent to/collected by the command center. At the fill event step 364A of FIG. 3A, data such as fill data, (364B) in FIG. 3B, can be sent to/collected by the command center.

In some implementations, the fill event can include a testing event and a registration event for registering the capsule in a database associated with the system described herein. After a capsule is filled, the testing event can include testing and analysis of the constituents of a carrier material filled in the capsule and the resulting information (e.g., in form of Certificate of Analysis) can be associated to the capsule, via the identifier added to the capsule and/or via the identifier store in a memory of the capsule. In some instances, the association of information regarding the carrier material in a capsule with the capsule, and the registration of the association can be following according to a compliance requisite by law.

Following the filling and testing events, in some implementations, the filler station can register the capsule by associating the identifier used to identify the capsule with another identifier of the capsule and/or with the identifier used to identify the carrier material filled in the capsule, and storing the association in the system (e.g., at a command center) for verification of the validity of the capsule. The filler station can perform registration of each capsule by authenticating a capsule (using the authentication key store in a capsule or by using the identifier attached to the capsule) and associating the identifier associated with the capsule packaging (e.g., QR code) with the capsule and/or with the identifier associated with the carrier material filled in the capsule.

At the filled capsule ship step 366A of FIG. 3A, data such as shipment inventory data and shipment tracking details, 366B in FIG. 3B, can be sent to/collected by the command center. At the pen ship step 368A of FIG. 3A, data such as shipment inventory data and shipment tracking details, 368B in FIG. 3B, can be sent to/collected by the command center. At the filled capsule sale step 370A of FIG. 3A, data such as sales transaction details, 370B in FIG. 3B, can be sent to/collected by the command center. At the pen sale step 372A of FIG. 3A, data such as sales transaction details, 372B in FIG. 3B, can be sent to/collected by the command center. At the user registration step 376A of FIG. 3A, data such as user registration data, 376B in FIG. 3B, can be sent to/collected by the command center. At the device registration step 378A of FIG. 3A, data such as device registration data, 378B in FIG. 3B, can be sent to/collected by the command center. At the vaporizer validation step 380A of FIG. 3A, data such as validation event data, 380B in FIG. 3B, can be sent to/collected by the command center. At the vaporizer use step 382A of FIG. 3A, data such as vaporizer use data 382B in FIG. 3B can be sent to/collected by the command center.

Figure 4:
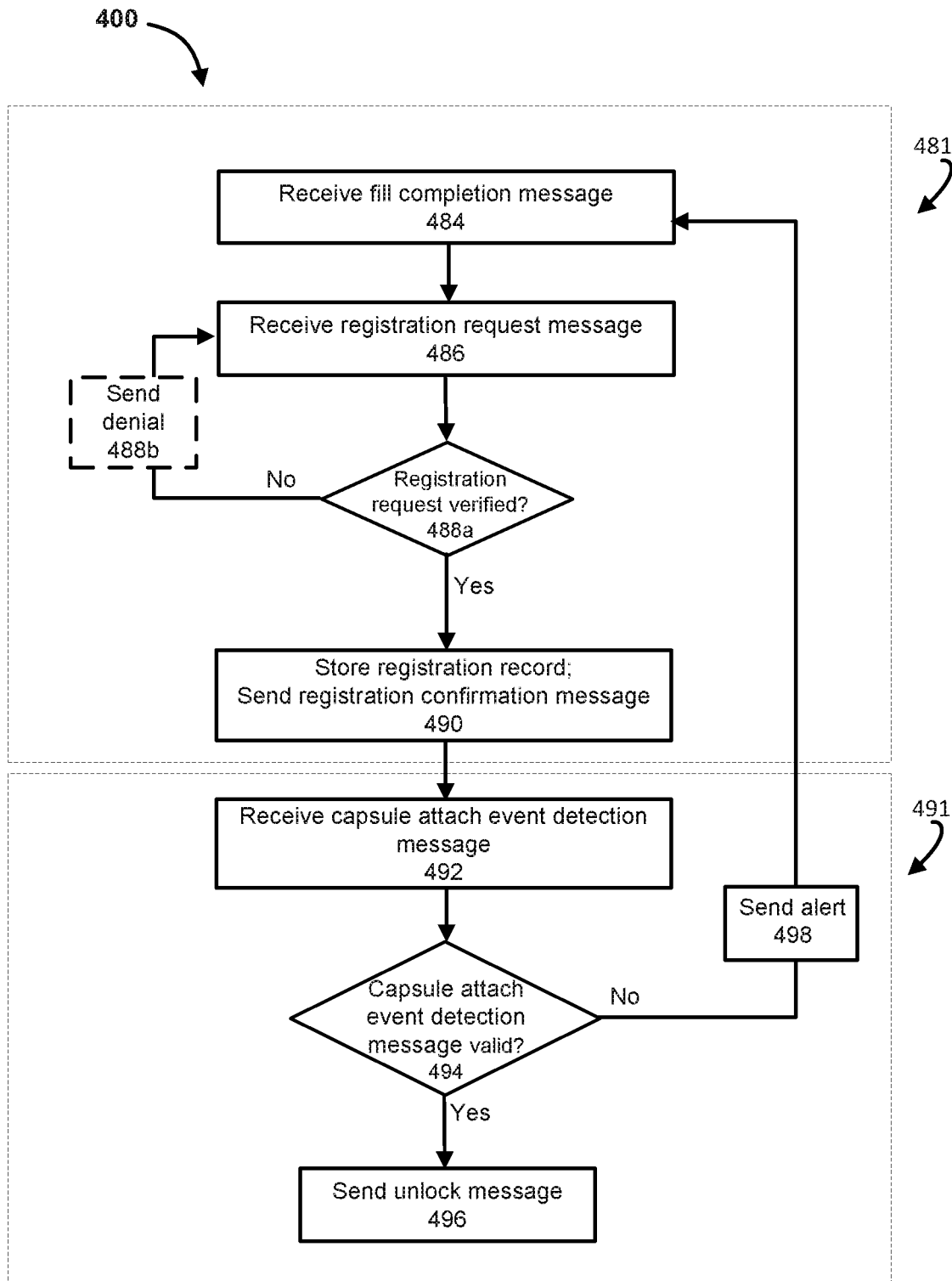
FIG. 4 illustrates a method of managing vaporizer security and/or traceability, in accordance with some embodiments.

FIG. 4 illustrates a processor-implemented method of managing vaporizer security and/or traceability, in accordance with some embodiments. The method 400 includes two portions 481 and 491 indicated by dashed boxes. The two portions may be performed together, one after another in any order, or independently.

As shown in FIG. 4, the method 400 includes the portion 481 that includes receiving, at 484, a fill completion message (e.g., from a filler station) indicating that a capsule has been filled, and specifying one or more of a capsule identifier and a carrier material identifier. The carrier material identifier can be cross-referenced, e.g., by a remote server (e.g., a command center), with related information such as provenance of the plant or pharmaceutical material that it includes, and/or processes that were used to extract, distill, or otherwise refine the plant or pharmaceutical material. At 486, the processor receives a registration request message 486 (e.g., from at least one of a vaporizer and a compute device of a user). At 488a, the processor assesses whether the registration request can be verified. If not, the processor can optionally send a denial message to the at least one of the vaporizer and the compute device, and the process reverts to step 486 to wait for another registration request message to be received. If the verification at 488a is successful, the processor generates and stores a registration record, and sends a registration confirmation message to the requestor (i.e., to the at least one of the vaporizer and the compute device).

The method 400 includes the portion 491, which includes the steps from 492 to 498. At 492, the processor receives a capsule attach event detection message, and determines, at 494, whether the capsule attach event detection message is valid. If not, the processor sends an alert message (at 498) to the requestor (i.e., to the at least one of the vaporizer and the compute device). If the capsule attach event detection message is deemed to be valid, the processor sends an unlock message, at 496, to the requestor (i.e., to the at least one of the vaporizer and the compute device).

In some embodiments, a vaporizer (whether disposable, as in FIG. 1A, or reusable, as in FIG. 1B) is identifiable, e.g., by virtue of one or more of the capsule identifier, carrier material identifier, or identifier(s) 123 (of FIGS. 1A and 1B), and includes an airflow sensor. The vaporizer can be configured to track (e.g., detect, store in a local memory, and/or cause to be stored in a remote memory by sending associated to a remote compute device) the number of inhalation events that have occurred, for example, since a particular capsule was installed onto the pen of the vaporizer, or since purchase (in the disposable case). By tracking material consumption (i.e., consumption of the carrier material through vaporization/inhalation events), the vaporizer can transmit or display to the user, and/or transmit to a remote server, consumption data. Alternatively or in addition, the vaporizer can limit a number of draws for that vaporizer or for a currently-installed capsule, such that once a predetermined number of draws have been taken/detected, the vaporizer is automatically disabled (e.g., by preventing activation of the heating coil). The function of limiting the number of draws can serve as a form of tamper-proofing and/or prevent the unauthorized refilling of the disposable vaporizer or capsule/cartridge. The vaporizer can also include an indicator thereon or therein, for example to indicate an amount of carrier material remaining in the capsule or disposable vaporizer. The amount of carrier material remaining in the capsule or disposable vaporizer can be determined based on the tracking described above. The function of providing an indication of remaining carrier material is particularly useful, for example, for implementations involving high-viscosity carrier materials whose volume can be difficult to ascertain using, for example, an observation window on the vaporizer.

In some embodiments, such as any of the embodiments described herein, a vaporizer (e.g., a vaporizer pen) can include a processor, an interface, heater control circuitry, a ransmitter, and a memory. The interface can be operably coupled to the processor and configured to operably and releasably couple a capsule including a capsule memory to the processor such that the processor can read the capsule memory. The heater control circuitry can be operably coupled to the processor and configured to heat carrier material included in the capsule. The transmitter can be operably coupled to the process and configured to communicate with a remote compute device and/or a remote server. A memory can be operably coupled to the processor and can store instructions to cause the processor to, in response to a capsule being coupled to the interface, read the memory of the capsule to identify a capsule identifier of the capsule. The memory can also store instructions to cause the processor to determine, via the processor and based on the capsule identifier, whether the capsule is authentic. If the capsule is determined to be authentic, the memory can also store instructions to cause the processor to send a signal from the processor to a remote compute device via the transmitter including an indication that the capsule identifier is authentic. If the capsule is determined to be not authentic, the memory can also store instructions to cause the processor to send a signal from the processor to the remote compute device via the transmitter including an alert.

In some embodiments, the memory can also store instructions to cause the processor to determine whether the capsule is authentic based on whether the capsule identifier includes a digital signature associated with a public key stored in the memory.

In some embodiments, the memory can also store instructions to cause the processor to activate the heater control circuitry in response to the processor determining that the capsule is authentic.

In some embodiments, the memory can also store instructions to cause the processor to write a recall identifier on the capsule memory in response to the processor receiving an indication that the capsule identifier is associated with a recall via the transmitter.

In some embodiments, the memory can also store instructions to cause the processor t In some embodiments, the memory can also store instructions to cause the processor to send, via the transmitter, a capsule attach event detection message in response to the capsule being coupled to the interface, and to activate the heater control circuitry only after receiving an unlock signal from the remote compute device.

The term "automatically" is used herein to modify actions that occur without direct input or prompting by an external source such as a user. Automatically occurring actions can occur periodically, sporadically, in response to a detected event (e.g., a user logging in), or according to a predetermined schedule.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

Some embodiments and/or methods described herein can be performed by software (executed on hardware), hardware, or a combination thereof. Hardware modules may include, for example, a general-purpose processor, a field programmable gate array (FPGA), and/or an application specific integrated circuit (ASIC). Software modules (executed on hardware) can be expressed in a variety of software languages (e.g., computer code), including C, C++, Java™ Ruby, Visual Basic™, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

Various concepts may be embodied as one or more methods, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments. Put differently, it is to be understood that such features may not necessarily be limited to a particular order of execution, but rather, any number of threads, processes, services, servers, and/or the like that may execute serially, asynchronously, concurrently, in parallel, simultaneously, synchronously, and/or the like in a manner consistent with the disclosure. As such, some of these features may be mutually contradictory, in that they cannot be simultaneously present in a single embodiment. Similarly, some features are applicable to one aspect of the innovations, and inapplicable to others.

In addition, the disclosure may include other innovations not presently described. Applicant reserves all rights in such innovations, including the right to embodiment such innovations, file additional applications, continuations, continuations-in-part, divisional s, and/or the like thereof. As such, it should be understood that advantages, embodiments, examples, functional, features, logical, operational, organizational, structural, topological, and/or other aspects of the disclosure are not to be considered limitations on the disclosure as defined by the embodiments or limitations on equivalents to the embodiments. Depending on the particular desires and/or characteristics of an individual and/or enterprise user, database configuration and/or relational model, data type, data transmission and/or network framework, syntax structure, and/or the like, various embodiments of the technology disclosed herein may be implemented in a manner that enables a great deal of flexibility and customization as described herein.

All definitions, as defined and used herein, should be understood to control over dictionary definitions, definitions in documents incorporated by reference, and/or ordinary meanings of the defined terms.

As used herein, in particular embodiments, the terms "about" or "approximately" when preceding a numerical value indicates the value plus or minus a range of 10%.

Where a range of values is provided, it is understood that each intervening value, to the tenth of the unit of the lower limit unless the context clearly dictates otherwise, between the upper and lower limit of that range and any other stated or intervening value in that stated range is encompassed within the disclosure. That the upper and lower limits of these smaller ranges can independently be included in the smaller ranges is also encompassed within the disclosure, subject to any specifically excluded limit in the stated range. Where the stated range includes one or both of the limits, ranges excluding either or both of those included limits are also included in the disclosure.

The indefinite articles "a" and "an," as used herein in the specification and in the embodiments, unless clearly indicated to the contrary, should be understood to mean "at least one."

The phrase "and/or," as used herein in the specification and in the embodiments, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the embodiments, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the embodiments, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of" or "exactly one of" "Consisting essentially of," when used in the embodiments, shall have its ordinary meaning as used in the field of patent law.

As used herein in the specification and in the embodiments, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the embodiments, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

While specific embodiments of the present disclosure have been outlined above, many alternatives, modifications, and variations will be apparent to those skilled in the art. Accordingly, the embodiments set forth herein are intended to be illustrative, not limiting. Various changes may be made without departing from the spirit and scope of the disclosure. Where methods and steps described above indicate certain events occurring in a certain order, those of ordinary skill in the art having the benefit of this disclosure would recognize that the ordering of certain steps may be modified and such modification are in accordance with the variations of the invention. Additionally, certain of the steps may be performed concurrently in a parallel process when possible, as well as performed sequentially as described above. The embodiments have been particularly shown and described, but it will be understood that various changes in form and details may be made.

The invention claimed is:

1. A method, comprising:
receiving, at a processor and from a fill station, a fill completion message including a formulation identifier and a first capsule identifier;
receiving, at the processor and from a compute device of a user, a registration request message including at least one of an identifier of the compute device or an identifier of the user;
receiving, at the processor and from the compute device of a user, an activation request message including a second capsule identifier and at least one of the identifier of the compute device or the identifier of the user, the second capsule identifier being the same as or different from the first capsule identifier;
determining, via the processor and based on at least one of the identifier of the compute device or the identifier of the user, whether the activation request message is valid;
if the activation request message is valid, sending an unlock message from the processor to the compute device, the compute device configured to provide an unlock instruction to a vaporizer in response to receiving the unlock message; and
if the activation request message is not valid, sending an alert from the processor to the compute device.

2. The method of claim 1, wherein the alert includes a signal to cause at least one of:
emission of an audio signal from the compute device;
display of an alert message via a graphical user interface (GUI) of the compute device; or
haptic feedback at the compute device.

3. The method of claim 1, further comprising:
verifying the registration request message, via the processor, based on a validity check of the at least one of the identifier of the compute device or the identifier of the user; and
storing, in a memory operably coupled to the processor, a registration record associating the user with the compute device.

4. The method of claim 3, further comprising:
sending, from the processor to the compute device and in response to verifying the registration request message, a registration confirmation message.

5. The method of claim 3, wherein the verifying the registration request message is based at least in part on a validity check of an age of the user.

6. The method of claim 1, wherein the determining whether the activation request message is valid includes determining whether a capsule associated with the second capsule identifier is disposed in a permissible geographic location for operation.

7. The method of claim 1, wherein the determining whether the activation request message is valid includes determining whether a capsule associated with the second capsule identifier includes a permissible substance for operation.

8. The method of claim 1, wherein the determining whether the activation request message is valid includes determining whether the second capsule identifier is associated with a recall indication.

9. The method of claim 1, wherein the determining whether the activation request message is valid is based on a user registration status.

10. The method of claim 1, wherein the determining whether the activation request message is valid includes determining that the activation request message is valid if the second capsule identifier matches the first capsule identifier.

11. A method, comprising:
storing, in a memory, a provenance record associating a first capsule identifier with capsule fill data;
receiving, at a processor and from a compute device, an activation request message including a second capsule identifier and at least one of an identifier of the compute device or an identifier of a user, the second capsule identifier being the same as or different from the first capsule identifier;
determining, via the processor and based on the provenance record, whether the activation request message is valid;
if the activation request message is valid, sending an unlock message to the compute device, the compute device configured to provide an unlock instruction to a vaporizer in response to receiving the unlock message; and
if the activation request message is not valid, sending an alert from the processor to the compute device.

12. The method of claim 11, wherein the determining whether the activation request message is valid includes determining that the activation request message is valid if the second capsule identifier matches the first capsule identifier.

13. The method of claim 11, further comprising:
storing, in the memory, a registration record associating the user with the compute device,
the determining whether the activation request message is valid further including determining that the activation request message is valid if the at least one of the identifier of the compute device or the identifier of the user match the registration record.

14. The method of claim 11, further comprising:
if the activation request message is valid, sending a provenance message to the compute device to cause display of provenance data via a GUI of the compute device.

15. An apparatus, comprising:
a processor; and
a memory operably coupled to the processor and storing instructions to cause the processor to:
receive, at the processor and from a remote compute device, an activation request message including a capsule identifier and at least one of an identifier of the remote compute device or an identifier of a user;
determine, via the processor and based on a registration record, whether the activation request message is valid;
if the activation request message is valid, send a signal including an unlock message from the processor to the remote compute device, the remote compute device configured to provide an unlock instruction to a vaporizer in response to receiving the signal; or
if the activation request message is not valid, send an alert from the processor to the remote compute device.

16. The apparatus of claim 15, wherein the processor determines whether the activation request message is valid based, at least in part, on whether the capsule identifier corresponds to a stored capsule identifier in the registration record.

17. The apparatus of claim 15, wherein the processor determines whether the activation request message is valid based, at least in part, on whether the identifier of the user is associated with a user age above a threshold age.

18. The apparatus of claim 15, wherein the processor determines whether the activation request message is valid based, at least in part, on whether a capsule associated with the capsule identifier of the activation request message is disposed in a permissible geographic location for operation.

19. The apparatus of claim 15, wherein the processor determines whether the activation request message is valid based, at least in part, on whether a capsule associated with the capsule identifier of the activation request message includes a permissible substance for operation.

20. The apparatus of claim 15, wherein the processor determines whether the activation request message is valid based, at least in part, on whether the capsule identifier is associated with a recall indication.

* * * * *